(12) United States Patent
Shan

(10) Patent No.: US 11,717,553 B2
(45) Date of Patent: Aug. 8, 2023

(54) COMBINED PLANT EXTRACT FOR GETTING RID OF MITES AND ACNE AND PREPARATION METHOD AND USE THEREOF

(71) Applicants: Nanjing Institute for Comprehensive Utilization of Wild Plants, All China Federation of Supply and Marketing, Jiangsu (CN); Shandong Jiuxin Biological Technology Co., Ltd, Shandong (CN)

(72) Inventor: Chengying Shan, Nanjing (CN)

(73) Assignees: Nanjing Institute for Comprehensive Utilization of Wild Plants, All China Federation of Supply and Marketing Corporation, Nanjing (CN); Shandong Jiuxin Biological Technology Co., Ltd, Tai'an (CN)

( * ) Notice: Subject to any disclaimer, the term of this patent is extended or adjusted under 35 U.S.C. 154(b) by 204 days.

(21) Appl. No.: 17/306,851

(22) Filed: May 3, 2021

(65) Prior Publication Data

US 2022/0110997 A1    Apr. 14, 2022

(30) Foreign Application Priority Data

Oct. 12, 2020    (CN) .......................... 202011083804.4

(51) Int. Cl.
| | | |
|---|---|---|
| *A61K 36/899* | (2006.01) | |
| *A61P 17/10* | (2006.01) | |
| *A61P 33/14* | (2006.01) | |
| *A61K 9/00* | (2006.01) | |
| *A61K 9/06* | (2006.01) | |
| *A61K 36/23* | (2006.01) | |
| *A61K 36/752* | (2006.01) | |
| *A61K 47/10* | (2017.01) | |
| *A61K 47/18* | (2017.01) | |
| *A61K 47/22* | (2006.01) | |
| *A61K 47/32* | (2006.01) | |

(52) U.S. Cl.
CPC .......... *A61K 36/899* (2013.01); *A61K 9/0014* (2013.01); *A61K 9/06* (2013.01); *A61K 36/23* (2013.01); *A61K 36/752* (2013.01); *A61K 47/10* (2013.01); *A61K 47/18* (2013.01); *A61K 47/22* (2013.01); *A61K 47/32* (2013.01); *A61P 17/10* (2018.01); *A61P 33/14* (2018.01); *A61K 2236/15* (2013.01); *A61K 2236/333* (2013.01)

(58) Field of Classification Search
None
See application file for complete search history.

(56) References Cited

U.S. PATENT DOCUMENTS 7,524,888 B2 * 4/2009 Coats ..................... A01N 43/16
424/DIG. 10

FOREIGN PATENT DOCUMENTS

CN          102669196 A  *  9/2012

* cited by examiner

*Primary Examiner* — Susan Hoffman
(74) *Attorney, Agent, or Firm* — Harness, Dickey & Pierce, P.L.C.

(57) ABSTRACT

The present disclosure provides a combined plant extract for getting rid of mites and acne obtained by ultrasound-assisted water extraction and alcohol precipitation of at least one of *Nepeta cataria*, bamboo, celery seeds, and orange peels. The preparation method of the present disclosure is simple and easy to operate, where extraction from effective parts of raw materials can be carried out sufficiently. The combined plant extract of the present disclosure was subjected to in vitro mite elimination experiments, and the results showed that it had excellent effects in getting rid of mites. Moreover, it is non-irritating to human skin and thus can be used directly or applied to formulations of daily chemicals to effectively help get rid of mites and acne.

4 Claims, 1 Drawing Sheet

COMBINED PLANT EXTRACT FOR GETTING RID OF MITES AND ACNE AND PREPARATION METHOD AND USE THEREOF

CROSS REFERENCE TO RELATED APPLICATION

This application claims the priority of Chinese Patent Application No. 202011083804.4, filed Oct. 12, 2020, which is incorporated herein by reference in its entirety.

FIELD

The present disclosure relates to a combined plant extract for getting rid of mites and acne and a preparation method and use thereof.

BACKGROUND

Acne, also known as "pimples", is a chronic inflammatory disease of the hair follicles and sebaceous glands mostly seen in young people aged 15-25. Often accompanied by seborrhea, acne has main clinical features such as pimples, papules and pustules. It may be treated by a medical technique or method.

According to recent studies, acne closely relates to mites. Human parasitic mites may be generally classified into two categories, the hair follicle mites and the sebaceous mites. Normally, the head and the facial skins are more likely to be infected by mites. The excretion of mites can clog pores to form blackheads, causing large pores in the skin and even inflammation over time. This may further cause a series of pathological changes such as acne, rosacea, and folliculitis, which greatly affect human health and facial beauty. Therefore, it is particularly important to get rid of mites during acne treatment.

Commonly used anti-mite products for eyes include products for external use such as a *Camellia sinensis* essential oil, a nitrazole cream, a benzyl benzoate emulsion, a permethrin cream, and a sulfur ointment, and products for oral administration such as metronidazole and ivermectin. However, these therapeutic products have many bad effects, for example, strong irritation (with e.g. the *Camellia sinensis* essential oil), vulnerability to allergies (with e.g. *Camellia sinensis* essential oil), drug resistance related to antibiotic drugs (e.g. Ivermectin). Moreover, they are cost-ineffective. Therefore, it is of great importance to develop a new product for getting rid of mites.

Acne, also known as "pimples", is a chronic inflammatory disease of the hair follicles and sebaceous glands mostly seen in young people aged 15-25. Often accompanied by seborrhea, acne has main clinical features such as pimples, papules and pustules. It may be treated by a medical technique or method.

According to recent studies, acne closely relates to mites. Human parasitic mites may be generally classified into two categories, the hair follicle mites and the sebaceous mites. Normally, the head and the facial skins are more likely to be infected by mites. The excretion of mites can clog pores to form blackheads, causing large pores in the skin and even inflammation over time. This may further cause a series of pathological changes such as acne, rosacea, and folliculitis, which greatly affect human health and facial beauty. Therefore, it is particularly important to get rid of mites during acne treatment.

Commonly used anti-mite products for eyes include products for external use such as a *Camellia sinensis* essential oil, a nitrazole cream, a benzyl benzoate emulsion, a permethrin cream, and a sulfur ointment, and products for oral administration such as metronidazole and ivermectin. However, these therapeutic products have many bad effects, for example, strong irritation (with e.g. the *Camellia sinensis* essential oil), vulnerability to allergies (with e.g. *Camellia sinensis* essential oil), drug resistance related to antibiotic drugs (e.g. Ivermectin). Moreover, they are cost-ineffective. Therefore, it is of great importance to develop a new product for getting rid of mites.

SUMMARY

A problem to be solved by the present disclosure is to propose an innovative solution to the above shortcomings in the prior art, especially a solution that can effectively help get rid of mites and prevent allergies.

In order to solve the above problem, the present disclosure adopts the following solutions. A combined plant extract for getting rid of mites and acne which is obtained by ultrasound-assisted water extraction and alcohol precipitation of at least one of *Nepeta cataria*, bamboo, celery seeds, and orange peels.

Further, according to the combined plant extract for getting rid of mites and acne in the above designed solution, the *Nepeta cataria*, the bamboo, the celery seeds, and the orange peels may be combined in a mass ratio of (30-60): (20-40):(10-30):(10-30), where the *Nepeta cataria* may be at least one of stems, leaves and flowers of *Nepeta cataria*, and the bamboo may be at least one of green outer skin, yellow internal part, and leaves of bamboo.

Further, according to the combined plant extract for getting rid of mites and acne in the above designed solution, the *Nepeta cataria*, the bamboo, the celery seeds, and the orange peels may be used in a mass ratio of 40:30:15:15.

Further, according to the combined plant extract for getting rid of mites and acne in the above designed solution, the *Nepeta cataria*, the bamboo, the celery seeds, and the orange peels may be used in a mass ratio of 60:20:10:10.

Further, according to the combined plant extract for getting rid of mites and acne in the above designed solution, the *Nepeta cataria*, the bamboo, the celery seeds, and the orange peels may be used in a mass ratio of 30:30:20:20.

Further, a method for preparing the combined plant extract for getting rid of mites and acne in the above designed solution includes the following steps: step a. crushing plants into granules, mixing in a determined ratio, adding an ethanol solution having a mass concentration of 60-80% in a material-to-liquid ratio of 1:(10-30); step b. ultrasonically shaking with an ultrasonic power of 200-300 W and a mixing liquid temperature of 50-70° C. for 60-120 min; step c. transferring to a water bath heating device, heating with a water bath until a system maintains slightly boiling, extracting for 2-4 h, filtering while hot, collecting a filtrate, and concentrating and distilling at a reduced pressure until a weight of the filtrate is equal to that of raw materials to obtain a concentrate as the combined plant extract for getting rid of mites and acne.

Further, use of the combined plant extract for getting rid of mites and acne according to the above designed solution in preparing daily chemicals is provided.

Further, use of the combined plant extract for getting rid of mites and acne according to the above designed solution in preparing daily chemicals is provided, where the daily chemicals may include aqueous solutions, essences, emulsions, creams, gels, powders, facial masks, handmade soaps, sprays, and wash and care products.

Further, use of the combined plant extract for getting rid of mites and acne according to the above designed solution in preparing daily chemicals is provided, where the combined plant extract for getting rid of mites and acne is added in an amount of 0.5-30% by mass fraction in the daily chemicals.

The present disclosure has the following technical effects. The present disclosure can provide a combined plant extract for getting rid of mites and acne and a preparation method and use thereof. The combined plant extract can be prepared from the following plants in parts by weight: 30-60 parts of *Nepeta cataria* (including stems, leaves and flowers), 20-40 parts of bamboo (including green outer skin, yellow internal part and leaves of bamboo), 10-30 parts of celery seeds and 10-30 parts of orange peels. In the present disclosure, the formula is based on the traditional Chinese medicine formulation theory so as to help get rid of mites and acne through synergistic effects of various natural plants. The combined plant extract can be prepared by an ultrasound-assisted ethanol extraction process, specifically, by crushing plants into granules, mixing in a determined ratio, adding an ethanol solution having a mass concentration of 60-80% in a material-to-liquid ratio of 1:(10-30); ultrasonically shaking with an ultrasonic power of 200-300 W and a temperature of 50-70° C. for 60-120 min; transferring to a water bath heating device, heating with a water bath until a system maintains slightly boiling, extracting for 2-4 h, filtering while hot, collecting a filtrate, and concentrating and distilling at a reduced pressure until a weight of the filtrate is equal to that of raw materials to obtain a concentrate as the combined plant extract for getting rid of mites and acne. The preparation method of the present disclosure is simple and easy to operate, where extraction from effective parts of raw materials can be carried out sufficiently. The combined plant extract of the present disclosure was subjected to in vitro mite elimination experiments, and the results showed that it had excellent effects in getting rid of mites. Moreover, it is non-irritating to human skin and thus can be used directly or applied to formulations of daily chemicals to effectively help get rid of mites and acne.

Among the raw materials for the combined plant extract provided by the present disclosure, *Nepeta cataria*, also known as catnip or catmint, is an annual herb widely found in China. It is mainly used for medicinal purposes and also used as a vegetable when it is young. Fresh plants thereof can be used to extract volatile essential oils which have been reported to have a strong insect repellent effect. Ethanol extract thereof contains nepetalactone and nepetalic acid and other substances. However, no other reports on activities of extracts thereof are seen. In an earlier experiment, the team for the present disclosure found that, the ethanol extract of *Nepeta cataria* had excellent in vitro mite eliminating and antibacterial activities.

Bamboo, also known as *Bambusoideae* or *Bambusaceae*, is a plant belonging to bamboo subfamily under the perennial grass family, and includes a wide range of varieties such as *Phyllostachys edulis, Dendrocalamus latiflorus* and *Fargesia spathacea*. A fresh bamboo has a green outer skin which may be called bamboo green, and a yellow part inside the bamboo which may be called bamboo yellow. In the present disclosure, leaves, green outer skin and yellow internal part of fresh bamboo can be used. A bamboo extract contains active ingredients such as flavonoids, phenolic acids and various amino acids, and its application in cosmetics has been reported. However, there is no report on use thereof in cosmetics for getting rid of mites and acne.

Celery, also named *Apium grauens* L. var. *dulcedc.*, is a plant belongs to the *Apiaceae* family. Having many varieties, it is one of the vegetables commonly consumed by Chinese people. It also has many functions such as calming liver and clearing heat, dispelling wind and dampness, and eliminating troublesome feeling and swelling. Celery seeds, mature seeds of celery, are very small in size, oval in shape, and mostly brown or dark brown in color. They contain eucalyptol, cymenolide, apigenin, linolenic acid, volatile oil and various minerals. Celery seeds are considered to have the effects of dispelling qi, reducing swelling, diuresis, opening blockage, and lowering blood pressure in traditional Chinese medicine.

An orange peel is an outer skin of the fruit of *Citrus sinensis* (L.) Osbeck. It can regulate qi, reduce phlegm, invigorate the stomach, and guide faeces out. An orange peel extract may contain hesperidin, limonene and other active components to balance the skin pH and benefit skin growth and repair to a certain extent.

Based on the traditional Chinese medicine formulation theory, the present disclosure includes the *Nepeta cataria* as the major component which has excellent mite eliminating and antibacterial effect, the bamboo as an associate component which has excellent anti-inflammatory and antibacterial effects, the celery seed as a facilitating component which can clear heat, dissipate qi, and eliminate stagnation, and the orange peel as an adjuvant component which harmonizes all the components, shows moisturizing, whitening and anti-allergic effects, and improves the skin pH at the acne affected area to promote skin repair. The 4 plant raw materials with various functions are combined to show a synergistic effect, where the extract thereof obtained by extraction with ethanol has special effects such as eliminating mites, inhibiting bacteria, clearing heat, anti-inflammation, reducing swelling and relieve itching. Moreover, the extraction and the separation methods are simple, and the obtained product has a high content of effective substances. The combined plant extract was tested for its physiological activity, and it was found that it had significant effects in getting rid of mites and acne.

DRAWINGS

DETAILED DESCRIPTION

Figure 1:
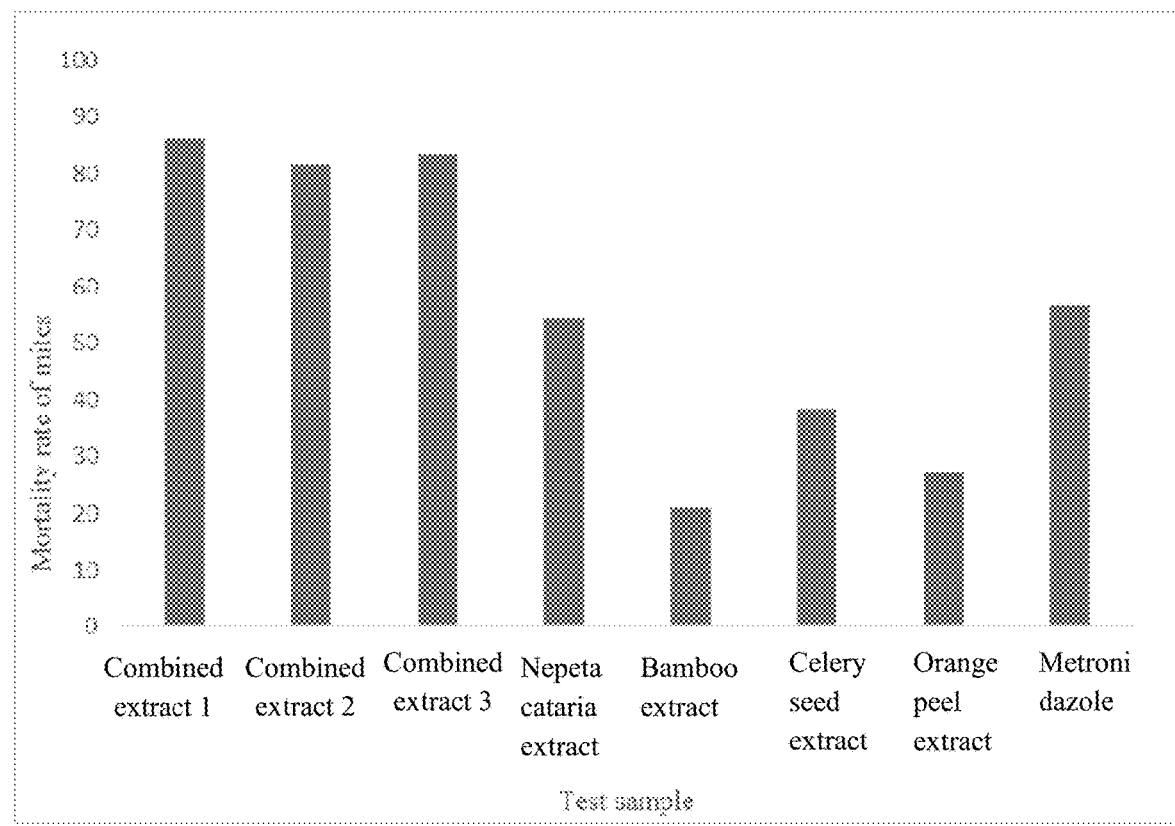
FIG. 1 shows a bar chart of the mortality rates of mites treated by combined plant extracts and single plant extracts.

The present disclosure is described in detail below with reference to the accompanying drawings.

The methods of the present disclosure are further described below with reference to specific embodiments, but the protection scope the present disclosure is not limited thereto. In the following embodiments, methods in the experiments are conventional methods unless otherwise specified; reagents and materials can be obtained from commercial sources unless otherwise specified.

Example 1 Preparation of Combined Plant Extract

*Nepeta cataria*, bamboo, celery seeds, and orange peels were mixed in an amount of 40 g, 30 g, 15 g, and 15 g respectively to obtain a mixture of 100 g. 2 kg of 70% ethanol solution was added. Then ultrasound shaking was carried out with an ultrasound power of 250 W and a temperature of 60° C. for 90 min. All materials were then transferred to a water bath heating device and heated with a water bath until the system maintained slight boiling. Continuous extraction was carried out for 3 h. After the extraction, filtering was carried out while hot to collect a filtrate. The filtrate was concentrated and distilled at a reduced pressure until the filtrate had a weight equal to that of the raw materials to obtain a concentrate as the combined plant extract of the present disclosure. The obtained combined plant extract was brown-yellow and gave a characteristic aroma of the original plants. The dry matter content of the extract was determined to be 7.22%.

Example 2 Preparation of Combined Plant Extract

*Nepeta cataria*, bamboo, celery seeds, and orange peels were mixed in an amount of 60 g, 20 g, 10 g, and 10 g respectively to obtain a mixture of 100 g. 1 kg of 80% ethanol solution was added. Then ultrasound shaking was carried out with an ultrasound power of 300 W and a temperature of 70° C. for 60 min. All materials were then transferred to a water bath heating device and heated with a water bath until the system maintained slight boiling. Continuous extraction was carried out for 2 h. After the extraction, filtering was carried out while hot to collect a filtrate. The filtrate was concentrated and distilled at a reduced pressure until the filtrate had a weight equal to that of the raw materials to obtain a concentrate as the combined plant extract of the present disclosure. The obtained combined plant extract was brown-yellow and gave a characteristic aroma of the original plants. The dry matter content of the extract was determined to be 7.04%.

Example 3 Preparation of Combined Plant Extract

*Nepeta cataria*, bamboo, celery seeds, and orange peels were mixed in an amount of 30 g, 30 g, 20 g, and 20 g respectively to obtain a mixture of 100 g. 3 kg of 60% ethanol solution was added. Then ultrasound shaking was carried out with an ultrasound power of 200 W and a temperature of 50° C. for 120 min. All materials were then transferred to a water bath heating device and heated with a water bath until the system maintained slight boiling. Continuous extraction was carried out for 4 h. After the extraction, filtering was carried out while hot to collect a filtrate. The filtrate was concentrated and distilled at a reduced pressure until the filtrate had a weight equal to that of the raw materials to obtain a concentrate as the combined plant extract of the present disclosure. The obtained combined plant extract was brown-yellow and gave a characteristic aroma of the original plants. The dry matter content of the extract was determined to be 7.56%.

Comparative Examples 1-4 Preparation of Single Plant Extracts 100 g of *Nepeta cataria*, 100 g of bamboo, 100 g of celery seeds, and 100 g of orange peels were taken respectively and marked as Comparative Examples 1-4 in the above order. The preparation method of Example 1 was used to prepare ethanol extracts of the *Nepeta cataria*, the bamboo, the celery seeds, and the orange peels corresponding to Comparative Examples 1-4 to obtain single plant extracts.

Example 4 In Vitro Experiment of Mite Elimination by Combined Plant Extracts and Single Plant Extracts 1 Materials and Methods
1.1 Experimental Materials Devices: artificial climate box (Japan Sanyo, MLR-350H), stereo microscope (Japan Olympus, SZ2), transparent tapes and other devices.

Mites for experiments: follicle mites were obtained with a transparent tape sticking overnight. Specifically, subjects were required to clean their face thoroughly and stick a transparent tape which is 6 cm long and 1.5 cm wide to their foreheads, cheeks, noses, chins or other sites before going to bed. The tape was peeled off the next day, stuck on a glass slide and observed under a microscope.

Preparation of samples to be tested: a total of 7 samples of combined plant extracts and single plant extracts prepared according to Examples 1-3 and Comparative Examples 1-4, were sequentially denoted as samples no. 1-7 to be tested, and diluted with deionized water to a 25% concentration for later use.

1.2 Experimental Methods 1.2.1 Test groups: the test solutions were denoted as no. 1-7 sequentially, a 2% metronidazole solution was used as the positive control group, and liquid paraffin was used as the blank control group. 10 follicle mites were included in each group. The experiment was repeated 3 times for each concentration of agent solutions, and the results were averaged.

1.2.2 Observation method: a micropipette was used to draw 200 μL of an agent solution and drop it on a slide. A push slide was used to spread the drop of solution evenly. The tapes where follicle mites were detected were stuck on the slides to allow sufficient contact of the solution and the mites. Then the slides were placed in an artificial climate box (at a temperature of 30° C. with humidity of 75%), and, 4 h later, observed for death of the follicle mites under the microscope.

1.2.3 Determination of death: the mites whose limbs or feet were immobile under a 400× microscope for 1 min were initially determined to be dead, and those who still immobile after 30 min were diagnosed as dead.

Corrected mortality rate/%=(number of surviving mites in the blank control group−number of surviving mites in a treatment group)/number of surviving mites in the blank control group×100

2. Results

TABLE 1

Corrected mite mortality rate for combined plant extracts and single plant extracts

| No. | Corrected mortality rate (%) ± SE |
|---|---|
| 1: combined extract (25%) | 86.33 ± 5.14 |
| 2: combined extract (25%) | 81.68 ± 6.31 |
| 3: combined extract (25%) | 83.42 ± 4.28 |
| 4: *Nepeta cataria* extract (25%) | 54.17 ± 5.26 |
| 5: bamboo extract (25%) | 21.04 ± 4.42 |
| 6: celery seed extract (25%) | 38.46 ± 5.05 |
| 7: orange peel extract (25%) | 27.16 ± 4.47 |
| Metronidazole group (2%) | 56.73 ± 4.07 |

FIG. 1 showed the mortality rates of mites treated by combined plant extracts and single plant extracts.

It can be seen from the results of Table 1 and FIG. 1 that, the combined plant extracts at a concentration of 25% significantly killed human follicle mites, where the mortality rates were 80-90%, significantly higher than that of the 2% metronidazole group as the positive control group. The 4 single plant extracts at a concentration of 25% had a certain killing effect on human follicle mites, where the mortality rates were 20-60%. It can be seen that the combined plant extracts prepared by the present disclosure had a significant mite killing effect, which was much better than that of the single plant extracts prepared in Comparative Examples 1-4. This indicated that a synergistic effect of various plant components was shown after combination.

Example 5 Experiment for Mortality Rates of Mites at Different Concentrations of the Combined Plant Extract 1 Materials and Methods
1.1 Experimental Materials
Devices: artificial climate box (Japan Sanyo, MLR-350H), stereo microscope (Japan Olympus, SZ2), transparent tapes and other devices.
Mites for experiments: follicle mites were obtained with a transparent tape sticking overnight. Specifically, subjects were required to clean their face thoroughly and stick a transparent tape which is 6 cm long and 1.5 cm wide to their foreheads, cheeks, noses, chins or other sites before going to bed. The tape was peeled off the next day, stuck on a glass slide and observed under a microscope.
Preparation of samples to be tested: The combined plant extract prepared according to Example 1 was diluted with deionized water to obtain final concentrations of 100%, 50%, 25%, 12.5%, 6.25%, and 3.125% for later use.
1.2 Experimental Methods
1.2.1 Test groups: the combined plant extract to be tested was divided into 6 concentration gradient groups, a 2% metronidazole solution was used as the positive control group, and liquid paraffin was used as the blank control group. 10 follicle mites were included in each group. The experiment was repeated 3 times for each concentration, and the results were averaged.
1.2.2 Observation method: a micropipette was used to draw 200 μL of an agent solution and drop it on a slide. A push slide was used to spread the drop of solution evenly. The tapes where follicle mites were detected were stuck on the slides to allow sufficient contact of the solution and the mites. Then the slides were placed in an artificial climate box (at a temperature of 30° C. with humidity of 75%), and, 4 h later, observed for death of the follicle mites under the microscope.
1.2.3 Determination of death: the mites whose limbs or feet were immobile under a 400× microscope for 1 min were initially determined to be dead, and those who still immobile after 30 min were diagnosed as dead.

Corrected mortality rate/%=(number of surviving mites in the blank control group−number of surviving mites in a treatment group)/number of surviving mites in the blank control group×100

2. Results

TABLE 2

Mortality rates of mites treated by the combined plant extract at different concentrations

| Group | Corrected mortality rate (%) ± SE |
|---|---|
| 100% in concentration | 100 |
| 50% in concentration | 95.16 ± 4.59 |

TABLE 2-continued

Mortality rates of mites treated by the combined plant extract at different concentrations

| Group | Corrected mortality rate (%) ± SE |
|---|---|
| 25% in concentration | 87.21 ± 5.28 |
| 12.5% in concentration | 72.34 ± 4.76 |
| 6.25% in concentration | 55.06 ± 6.13 |
| 3.125% in concentration | 38.14 ± 5.41 |
| 2% metronidazole group | 54.66 ± 4.38 |

Figure 2:
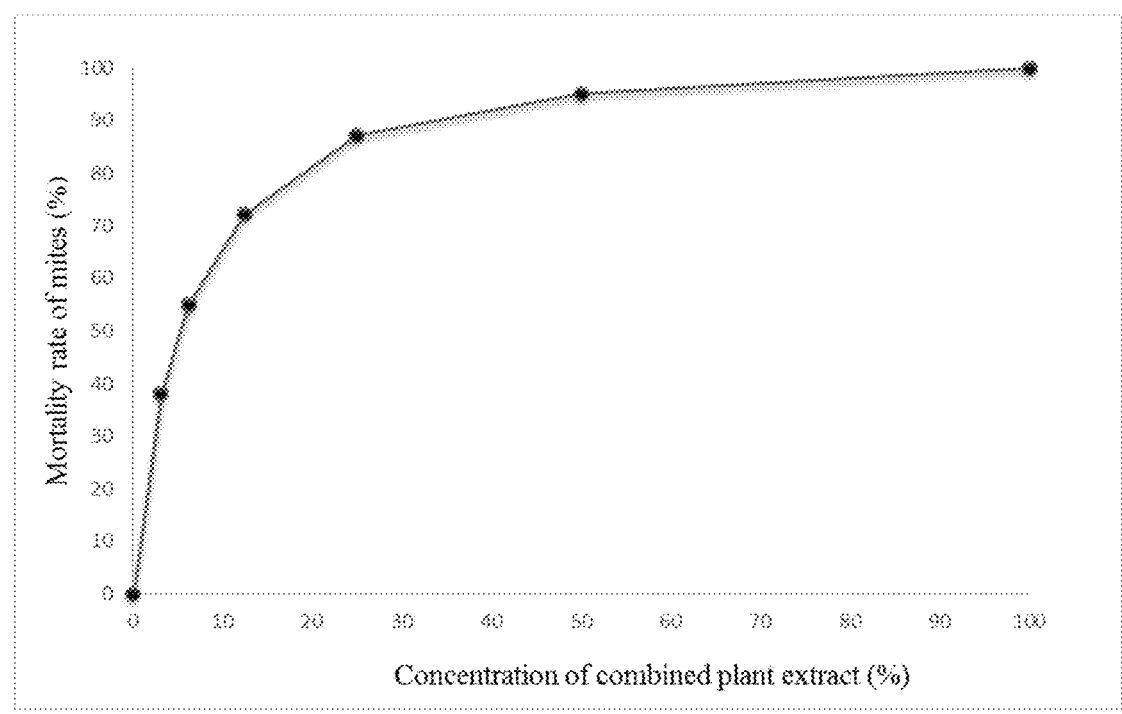
FIG. 2 shows the curve of mortality rates of mites at different concentrations of the combined plant extract.

It can be seen from the results of Table 2 and FIG. 2 that, the combined plant extract prepared in Example 1 had a significant killing effect on human follicle mites, which increased with the concentration. It can be seen from the curve that, when the concentration of the combined plant extract was 50%, the morality rate of mites was close to 100%, and when the concentration was 10%, the morality rate was about 60%. The combined plant extract had a lethal concentration 50% ($LC_{50}$) of less than 8%. The experiments fully proved that the combined plant extract had an extremely significant killing effect on human follicle mites. When the combined plant extract was used in daily chemicals such as cosmetics, more than 8 g of the combined plant extract was recommended to be added for each 100 g of the preparation.

Example 6 Preparation of a Gel for Getting Rid of Mites and Acne with the Combined Plant Extract as the Main Effective Component A gel for getting rid of mites and acne with the combined plant extract as the main effective component was prepared with the formula shown in Table 5.

TABLE 5

Formula of the gel for getting rid of mites and acne

| Component | Content (%) |
|---|---|
| Combined plant extract | 10 |
| Glycerin | 5 |
| 1,3-butanediol | 5 |
| Vitamin B3 | 2 |
| *Hamamelis mollis* extract | 1.5 |
| Carbomer U20 | 1.0 |
| Triethylamine (TEA) | 1.0 |
| Fragrance | 0.05 |
| Phenoxyethanol | 0.3 |
| Deionized water | As balance |

Preparation process: the combined plant extract, the vitamin B3, the *Hamamelis mollis* extract and the carbomer U20 were added with an appropriate amount of deionized water, heated and stirred to 75° C. to achieve full dissolution, and kept at this temperature for 20-30 min. Then, the glycerin, the 1,3-butanediol and the fragrance were added, stirred for dissolution at a maintained temperature to achieve a transparent state. Deionized water was added as balance. After uniform dissolution, the temperature was cooled to about 45° C. The TEA and the phenoxyethanol were added, stirred uniformly, and allowed to stand still for cooling down to obtain a gel for getting rid of mites and acne.

The gel for getting rid of mites and acne is a representative embodiment of the combined plant extract prepared in the present disclosure as a daily chemical product for getting rid of mites and acne. The combined plant extract can also be prepared into aqueous solutions, emulsions, creams, powders, facial masks, handmade soaps, sprays, wash and care products and other daily chemicals for getting rid of mites and acne based on commonly used formulas in the daily chemical industry.

Example 6 Evaluation of Effect of the Gel for Getting Rid of Mites and Acne

Subjects for evaluation: 56 young persons aged 15-25 with acne on the face were selected, including 28 males and 28 females.

Evaluation method: the double-blind method was used. The gel for getting rid of mites and acne prepared in Example 5 was applied 3 times in the morning, at noon and in the evening every day for 28 d as a course of treatment.

Evaluation criteria: (1) significant effect: acne was reduced by more than 70%; (2) certain effect: acne was reduced by more than 30%; (3) no effect: acne was reduced by less than 30%.

Evaluation results: 33 persons had a significant effect, accounting for 58.9%; 14 had a certain effect, accounting for 25%; 9 had no effect, accounting for 16.1%. The total effective rate reached 83.9%, and none of the persons reported adverse reactions such as skin allergies, redness and swelling. This indicated that the combined plant extract for getting rid of mites and acne in the present disclosure had a desired effect in getting rid of acne.

The foregoing embodiments are preferred embodiments of the present disclosure. However, the embodiments of the present disclosure are not limited by the foregoing embodiments. Any other changes, modifications, replacements, combinations and simplifications made without departing from the spirit and principle of the present disclosure should all be equivalent replacement manners, and fall within the protection scope of the present disclosure.

What is claimed is:

1. A combined plant extract for killing mites and removing acne, wherein the combined plant extract is obtained by ultrasound-assisted water extraction and alcohol perception of *Nepeta cataria*, bamboo, celery seeds, and orange peels, wherein, the *Nepeta cataria*, the bamboo, the celery seeds, and the orange peels are combined in a mass ratio of (30-60):(20-40):(10-30):(10-30), the *Nepeta cataria* is at least one of stems, leaves and flowers of *Nepeta cataria*, and the bamboo is at least one of green outer skin, yellow internal part, and leaves of bamboo.

2. The combined plant extract for killing mites and removing acne according to claim 1, wherein the *Nepeta cataria*, the bamboo, the celery seeds, and the orange peels are used in a mass ratio of 40:30:15:15.

3. The combined plant extract for killing mites and removing acne according to claim 1, wherein the *Nepeta cataria*, the bamboo, the celery seeds, and the orange peels are used in a mass ratio of 60:20:10:10.

4. The combined plant extract for killing mites and removing acne according to claim 1, wherein the *Nepeta cataria*, the bamboo, the celery seeds, and the orange peels are used in a mass ratio of 30:30:20:20.

* * * * *